United States Patent [19]

Monnier

[11] 4,401,115
[45] Aug. 30, 1983

[54] RESPIRATOR APPLIANCES

[75] Inventor: Jean-Pierre Monnier, Maurepas, France

[73] Assignee: L'Air Liquide, Societe Anonyme pour L'Etude et L'Exploitation des Procedes Georges Claude, Paris, France

[21] Appl. No.: 266,480

[22] Filed: May 22, 1981

[30] Foreign Application Priority Data

Jun. 10, 1980 [FR] France ............... 80 12824

[51] Int. Cl.³ .................................. A61M 15/00
[52] U.S. Cl. ..................... 128/204.23; 128/204.25; 128/204.26; 128/205.13; 128/205.24
[58] Field of Search ............... 128/204.21, 204.23, 128/204.24, 204.25, 204.26, 205.13, 205.28

[56] References Cited

U.S. PATENT DOCUMENTS

| | | | |
|---|---|---|---|
| 3,357,428 | 12/1967 | Carlson | 128/204.23 |
| 3,952,739 | 4/1976 | Cibulka | 128/204.23 |
| 3,974,828 | 8/1976 | Bird | 128/204.25 |
| 4,020,834 | 5/1977 | Bird | 128/204.25 |
| 4,206,754 | 6/1980 | Cox et al. | 128/204.23 |
| 4,224,940 | 9/1980 | Monnier | 128/205.16 |
| 4,340,044 | 7/1982 | Levy et al. | 128/204.21 |

FOREIGN PATENT DOCUMENTS

1432572 of 0000 United Kingdom .

*Primary Examiner*—Kyle L. Howell
*Assistant Examiner*—Mitchell J. Shein
*Attorney, Agent, or Firm*—Lee C. Robinson, Jr.

[57] ABSTRACT

This invention relates to a respirator provided with a supply circuit and a utilization circuit, with a breathable gas accumulator, a distributor and a cyclic action control device.

The respirator comprises an auxiliary make-up circuit for providing a make-up or complement of breathable gas, a discharge circuit for the breathable gas and a ventilation corrector device sensing the pressure in the utilization circuit and acting on said make-up circuit and discharge circuit to provide a complement or withdrawal of breathable gas.

The invention is applicable for treatment of respiratory inadequacies performed in hospital or domestic environments.

9 Claims, 6 Drawing Figures

RESPIRATOR APPLIANCES

BACKGROUND OF THE INVENTION

The present invention relates to respirator appliances for the artificial ventilation of the pulmonary tracts of a user in accordance with a cycle of inspiratory and expiratory stages, of the kind comprising a supply circuit delivering a breathable gas, a utilisation circuit comprising an inhalation branch and an exhalation branch provided with an exhalation valve, a breathable gas accumulator forming a reserve buffer, a distributor connected to said supply circuit and comprising an inhalation valve in communication with said inhalation branch, an accumulator valve and a non-return valve which are both in communication with said accumulator, a cyclic-action control device which operates said inhalation outflow and accumulator valves according to a predetermined programme, and which is arranged to direct the breathable gas coming from the supply circuit and from said accumulator towards the inhalation branch during the inflow or breathing in stages, and the breathable gas coming from said supply circuit towards said accumulator during the exhalation stages. Hereinafter, such as respirator will be referred to as "of the kind described".

Respirators of the kind described in which the breathable gas is stored during the exhalation stage and then restored to the utilising circuit during the inhalation stage, are intended primarily for treatment of respiratory deficiencies or failures and may be utilised in hospital and home environments, or else as an emergency service.

The cyclic action control device renders it possible to supply the user with a ventilation, that is to say a given volume of breathable gas per unit of time, the parameters of which, in particular the frequency of the breathing cycles, the inhalation and exhalation periods and the ratio between these inflow and outflow periods, are displayed and modifiable at will. The ventilating operation may consequently easily be verified and controlled by the operative entrusted with the operation of the respirator, who is commonly a doctor.

French Patent Specification No. 76.07.945 filed Mar. 19, 1976, under the title "Respirator" describes a respirator of the kind described which is arranged adapt itself automatically to the pulmonary compliance and resistance of the user.

Exhaustive research performed in the sphere of artificial ventilation brought to light a particular number of problems which arise in medical practice, and the shortcomings of particular existing appliances. These problems are encountered mainly in two cases:

(a) that in which the ventilation controlled by the operative becomes inadequate for the patient, and (b) That in which this ventilation becomes excessive for the patient, for example due to an obstruction of his pulmonary tracts during treatment.

SUMMARY OF THE INVENTION

It is an object of the invention substantially to eliminate or minimise these problems and to this end proposes a respirator of the kind described but which complementarily comprises an auxiliary make-up or replenishment circuit for providing an increment of breathable gas to the utilisation circuit, a discharge circuit for withdrawing a part of the breathable gas from said utilisation circuit and a ventilation corrector device sensing the pressure changes in the inhalation branch of the utilisation circuit and the inhalation and exhalation periods, said corrector device controlling said make-up and discharge circuits to provide a "topping-up" or a discharge of breathable gas, respectively, as a function of said changes and of said periods.

A respirator according to the invention consequently renders it possible to increase or decrease the ventilation substantially automatically, as a function of the pressure in the utilisation circuit, which depends on the patient, that is to say on his reactions or condition.

According to another feature of the invention, the aforesaid auxiliary topping-up circuit comprises a duct connecting the supply circuit to the accumulator and provided with an electromagnetic valve and with a calibrated orifice.

The complementary supply of breathable gas to the utilisation circuit is thus provided via the accumulator at a rate of flow the value of which is a function of the calibrated orifice and of the period of opening of the electromagnetic valve.

According to yet another feature of the invention, the aforesaid discharge circuit comprises a passage for venting to the atmosphere, which passage is in communication with the accumulator and is fitted with an electromagnetic valve.

The discharge of breathable air present in excessive volume is thus performed from the accumulator, in verifiable manner due to the electromagnetic valve.

BREIF DESCRIPTION OF THE DRAWINGS

In order that the invention may be more clearly understood, reference will now be made to accompanying drawings which show certain embodiments thereof by way of example, in conjunction with some explanatory graphs, and in which:

FIG. 1 is a graph which, as a function of the time t, shows the value of the pressure p in the utilisation circuit of a respirator of known kind, in the case in which the ventilation provided by the said respirator becomes inadequate, FIG. 2 is a graph identical to that of FIG. 1, but relating to the case in which the ventilation provided becomes excessive, FIG. 3 illustrates diagramatically a respirator in accordance with the invention, FIG. 4 illustrates the ventilation corrector device to enlarged scale and in more detailed manner, FIG. 5 is a graph identical to that of FIG. 1, but plotted with the respirator in accordance with the invention, FIG. 6 is a graph identical to that of FIG. 2, but plotted with the respirator in accordance with the invention.

DETAILED DESCRIPTION OF PREFERRED EMBODIMENTS

Figure 1:
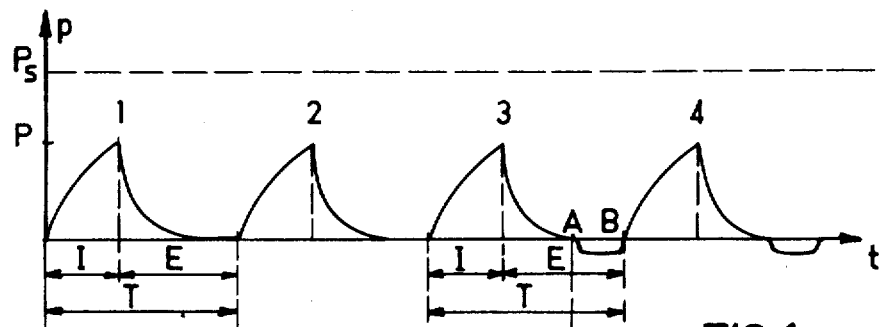

Referring now to the drawings and firstly to FIG. 1, it will be apparent therefrom that the pressure in the utilisation or patient's circuit rises during the period I of the inflow or inhalation stage or time from a value assumed as an origin (residual pulmonary pressure) to a maximum pressure P, and then drops during the period E of the exhalation or outflow stage or time, to the original value, the sum of these periods being the breathing period $T(I+E=T)$. It should be observed that the pressure in the utilisation circuit cannot exceed a safety value Ps in any event, and this is due to a safety valve incorporated in the circuit. The values I,E,T as well as the volume of insufflated gas, are controlled in such manner that they correspond to the needs and characteristics of the patient. The value of P is the result of this controlling operation. The corresponding breathing cycles are illustrated at 1 and 2.

If the ventilation becomes inadequate following alterations of the characteristics of the patient, the latter reacts with an attempt to inhale during the exhalation stage, that is to say between the instant (A) in which he has completed an exhalation and the onset of the following inhalation stage (B) imposed by the respirator. This inhalatory effort generates a negative pressure in the patient's circuit, between A and B, which manifests a ventilation inadequacy (cycles 3 and 4).

Figure 2:
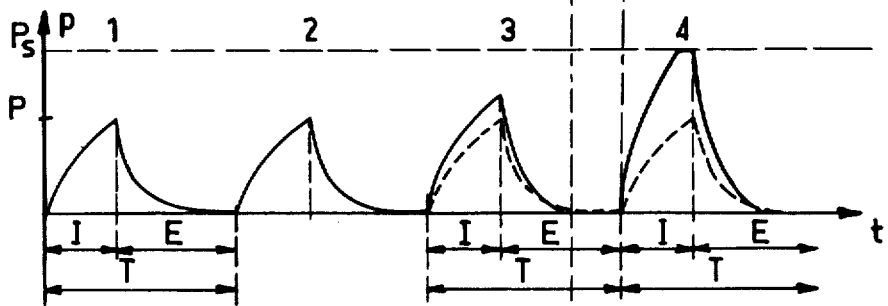

FIG. 2, in which the same references denote the same parameters as in FIG. 1, relates to the case of a patient whose pulmonary tracts are obstructed. The pressure rises considerably in the patient's circuit, during a first period (cycle 3). This is manifested by an increase in the energy level in the accumulator and by a pressure rise which is continuous during each cycle until it reaches the value of the safety pressure Ps (cycle 4). The ventilation provided by the respirator is excessive.

Figure 3:
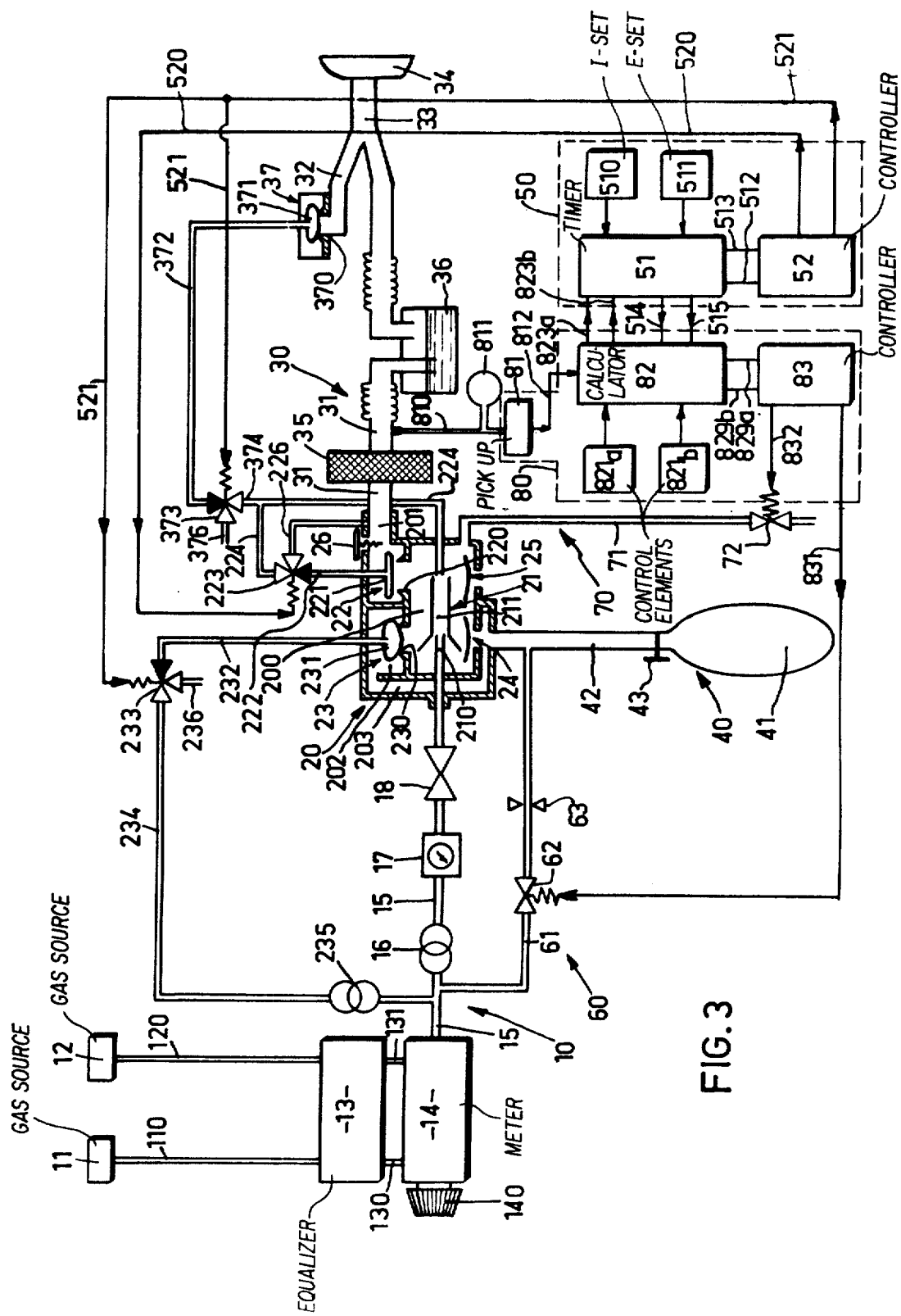

According to the embodiment illustrated in FIG. 3, a respirator according to the invention essentially comprises a circuit 10 for supplying breathable gas, a distributor block 20, utilisation or patient's circuit 30, a pneumatic accumulator 40, this circuit 30 and this accumulator receiving the breathable gas from the circuit 10 via the distributor 20, and a cyclic action electrical control device 50 which has the task of verifying the successive inhalation and exhalation cycles and of assuring the breathing of the patient.

The supply circuit 10 comprises two sources 11 and 12 of gas under pressure, for example being a source of air and a source of oxygen in the case in which the patient should undergo forced breathing with superoxygenated air.

The sources 11 and 12 are in communication via pipes 110 and 120 with a pressure equaliser 13 which, for its part, is in communication via pipes 130 and 131 with a mixer 14 fitted with a control knob 140 which allows the mixing of the two gases to be metered.

The mixer 14 is in communication via a pipe 15 fitted with a pressure regulator 16 which restores the gas pressure to a stable value, of the order of 1 bar, with a flow-meter 17 and with a flow control valve 18.

The distributor 20 comprises a venturi tube 21 having an injector 210 connected to the pipe 15 for receiving the breathable gas and having a divergent section 211 which leads directly into an inner space 200 of the distributor. The said space 200 is in communication with the utilisation circuit 30 via an inhalation valve 22 housed in a compartment 201, with the accumulator 40 via an accumulator valve 23 housed in a compartment 202 in communication with a passage 203 on the one hand and on the other hand via a non-return valve 24 (letting the gas pass through in the direction from the accumulator 40 towards the circuit 30), and finally with the atmosphere via a complementary air or venting valve 25. The compartment 201 is in communication with the atmosphere via a calibrated valve 26 which prevents the pressure in the circuit 30 from exceeding the safety value Ps.

The inhalation valve 22 comprises a seat 220, a pneumatic valve 221 connected via a pipe 222 to an electromagnetic valve 223 acting to "inflate" and "deflate" the said pneumatic valve and in communication for this purpose via a pipe 224 with the outlet of the divergent section 211 of the venturi tube 21 on the one hand, and on the other hand via a pipe 226 with the compartment 201 of the distributor 20.

The accumulator valve 23 comprises a seat 230, a pneumatic valve 231 which is in communication via a pipe 232 with an electromagnetic valve 233 for raising and lowering said pneumatic valve. The electromagnetic valve 233 is in communication via a pipe 234 provided with a regulator 235 with the pipe 15 on the one hand, and on the other hand with the atmosphere via a bleed 236.

The utilising circuit 30 comprises an inhalation branch 31 which is in direct communication with the compartment 201 of the distributor 20 and an exhalation branch 32, these two branches 31 and 32 being in communication via a common trunk 33 with a mask 34 for the patient. The branch 31 comprises a bacteriological filter 35 and a humidifier 36. The exhalation branch 32 is in communication with the atmosphere via an exhalation valve 37. The exhalation valve 37 comprises a seat 370, a pneumatic valve 371 which is in communication via a pipe 372 with an electromagnetic valve 373 for raising and lowering said pneumatic valve. The electromagnetic valve 373 is connected on the one hand to the outlet of the divergent section 211 via a pipe 374 and the aforesaid pipe 224 of the inhalation valve, and on the other hand with the atmosphere via a bleed 376.

The accumulator 40 comprises an elastic bladder 41 referred to as an integrating bladder, incorporated to store a part of the breathable gas, thus establishing a reserve buffer, and which is connected to the distributor 20 via a pipe 42 fitted with a safety valve 43.

The control device 50 essentially comprises an electronic clock or timer 51 and a control element 52 formed, for example, by a power amplifier and driven by said clock via conductors 512 and 513. The device 50 is arranged for controlling, according to a preset programme, the frequency of the breathing cycles 1/I+E and the ratio I/E of the inhalation period over the exhalation period for each breathing cycle, this frequency and ratio being adjustable by means of control elements 510 and 511 respectively, for example formed by potentiometers and co-ordinated with the clock 51. The control element 52 is connected via a conductor 520 to the electromagnetic valve 223 and via a common conductor 521 to the electromagnetic valves 223 and 373 and is arranged to transmit signals to the said electromagnetic valves in dependance upon the driving signals it receives from the clock 51, which operate their opening and closing and consequently the opening and closing of the pneumatic valves 22, 23 and 37.

The operative (i.e. attendant, nurse, paramedic, etc.) may consequently treat the patient by establishing a sequence of particular inhalation and exhalation periods.

The respirator according to the invention comprises an auxiliary make-up or topping-up circuit 60, a discharge circuit 70 and a ventilation corrector device 80, apart from the components hereinabove referred to.

The auxiliary make-up circuit 60 essentially comprises a pipe 61 provided with an electromagnetic valve 62 operating on the all or nothing (open/close) principle, and with a calibrated orifice 63. The pipe 61 establishes a direct connection between the pipe 15 of the supply circuit 10 and the pipe 42 of the accumulator 40.

This discharge circuit 70 comprises a venting pipe 71 connected to the inner space 200 of the distributor 20 and provided at its end with an electromagnetic valve 72 operating on the all or nothing principle.

The inventilation corrector device 80 comprises a pressure sensor or pickup 81, an electronic calculator 82 sensing the readings of said pickup, and a control element 83 driven by the calculator.

The pickup 81, may, for example, be of the piezo-resistive type, and is connected by a pipe 810 provided with a pressure gauge 811 to the inhalation branch 31, and it detects the pressure in this branch and supplies the calculator 82 via an electrical conductor 812 with an electrical voltage proportional to said pressure.

The calculator 82 is arranged to control the clock 51, in such manner that when the pressure in the branch 31 reaches a preset minimum value Pm (negative pressure) or a preset maximum value PM (lower or at most equal to the safety pressures Ps), the said clock initiates a premature inhalation or exhalation stage, that is to say one preceding the inhalation or exhalation stage which would normally have occurred in accordance with the programme determined by the control elements 510 and 511. As a matter of fact, the elements 510 and 511 establish the frequency 1/I+E of the breathing cycles as well as the ratio I/E between the inhalation and exhalation periods, and consequently determine I and E. The fact of triggering an inhalation or exhalation stage in advance has the result of shortening the exhalation or inhalation period of the programmed breathing cycle, these two periods then assuming values Er and Ir, lower than E and I, respectively.

The calculator 82 is also arranged to store the periods I and E and for establishing the differences E−Er and I−Ir, in such manner as to control the period of opening of the valves 62 and 72 as a function of these chronological differences E−Er and I−Ir.

Figure 4:
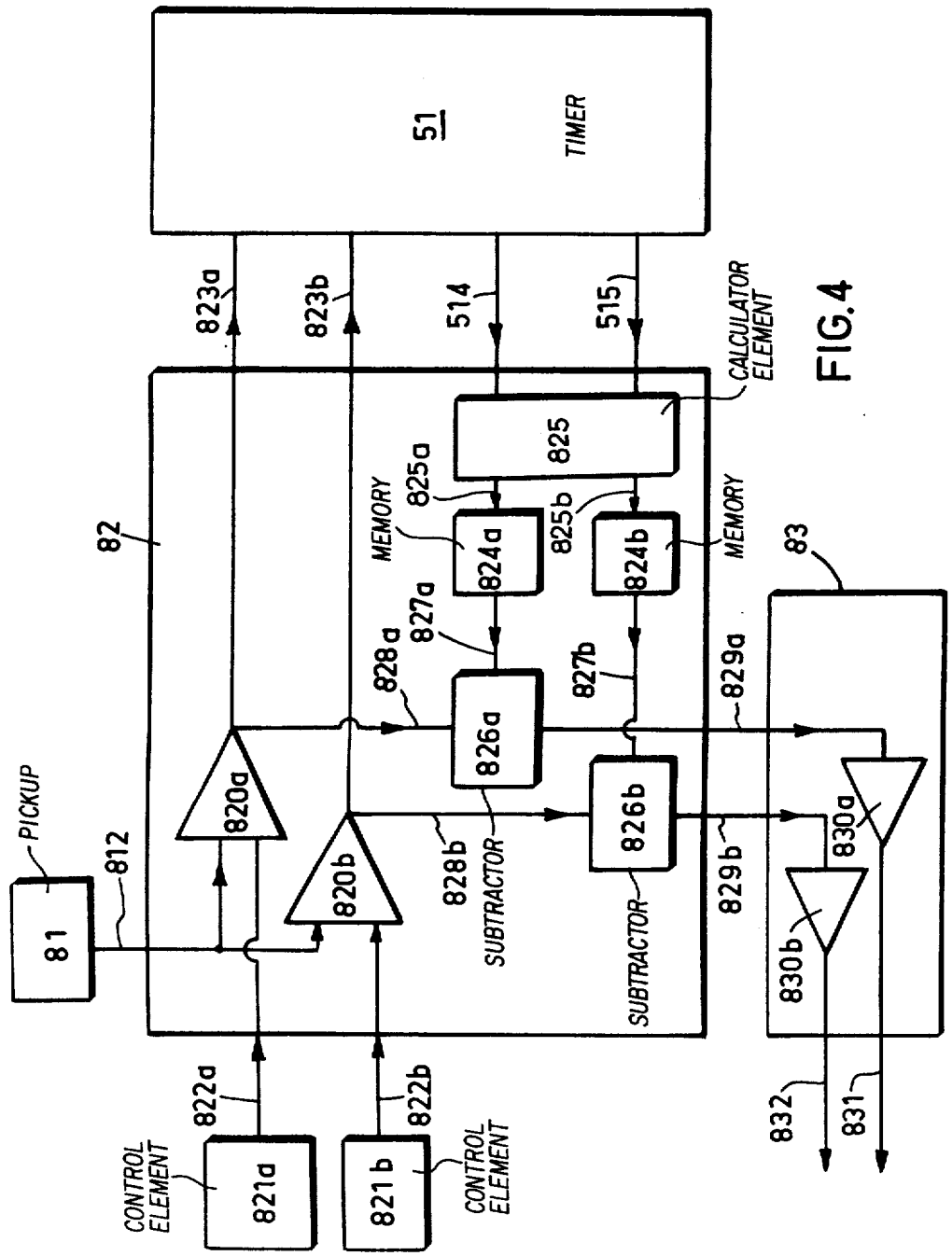

The calculator 82, as shown in FIG. 4, comprises two comparator circuits 820a and 820b for comparing the electrical voltages supplied by the pickup 81 to two reference voltages, one of these being a minimum corresponding to the minimum pressure Pm, the other a maximum corresponding to the maximum pressure PM. These two reference pressures, and consequently the two pressures Pm and PM may be selected at will by the operative (with the condition PM<Ps) by adjusting control elements 821a and 821b, for example formed by potentiometers and connected via conductors 822a and 822b to one of the input terminals of each of the comparators. The comparators 820a and 820b have their other input terminals connected to the output terminal of the pickup 81 via a conductor 812 and have their output terminals connected via conductors 823a and 823b, to the time base (not shown) of the clock 51.

The calculator 82 also comprises two memory circuits 824a and 824b and two subtractor circuits 826a and 826b. At their input terminals, the circuits 824a and 824b receive the periods I and E programmed by the clock 51, and store these.

These periods I and E are calculated by a calculator element 825 connected by conductors 514 and 515 to the circuits (not shown) of the clock 51, which provide the values 1/I+E and I/E, and are transmitted to the memories 824a and 824b via the conductors 825a and 825b. The subtractors 826a and 826b receive, on the one hand, the periods I and E from the memories 824a and 824b via conductors 827a and 827b, and on the other hand the periods Ir and Er from the comparators 820a and 820b via conductors 828a and 828b. The differences I−Ir and E−Er are transmitted via conductors 829a and 829b to the control element 83.

The control element 83 comprises two amplifiers 830a and and 830b the input terminals of which are connected to the subtractors 826a and 826b via the aforesaid conductors 829a and 829b, their output terminals being connected to the electromagnetic valves 62 and 72 via conductors 831 and 832 respectively, to operate the opening and closing of the said electromagnetic valves as a function of the signals they receive from the subtractors 826a and 826b.

The operation of the distributor described above is as follows:

The valves 22, 23 and 37 controlled by the control device 50 cause an inhalation cycle or an exhalation cycle, depending on whether they are open or closed. During inhalation (case shown in FIG. 3) the valve 22 is open and the valves 23 and 37 are closed. The breathable gas coming from the supply circuit 10 via the venturi tube 21 and that coming from the bladder 41 via the non-return valve 24 pass from the inner space 200 into the compartment 201 of the distributor 20, then into the branch 31 of the utilisation circuit 30. During exhalation, the valve 22 is closed and the valves 23 and 37 are open. The gas exhaled by the patient passes into the atmosphere via the exhalation branch 32 and the valve 37 whereas the breathable gas coming from the supply circuit 10 via the venturi tube 21 passes from the inner space 200 to the bladder 41 via the compartment 202, the passage 203 and the pipe 42. If the ventilation thus provided for the patient is compatible in frequency and volume with the patient's pulmonary requirements and characteristics, that is to say if this ventilation occurs according to cycles 1 and 2 of FIGS. 5 and 6, the electromagnetic valves 62 and 72 co-ordinated with the make-up circuit 60 and the discharge circuit 70 are kept closed by the corrector device 80.

Figure 5:
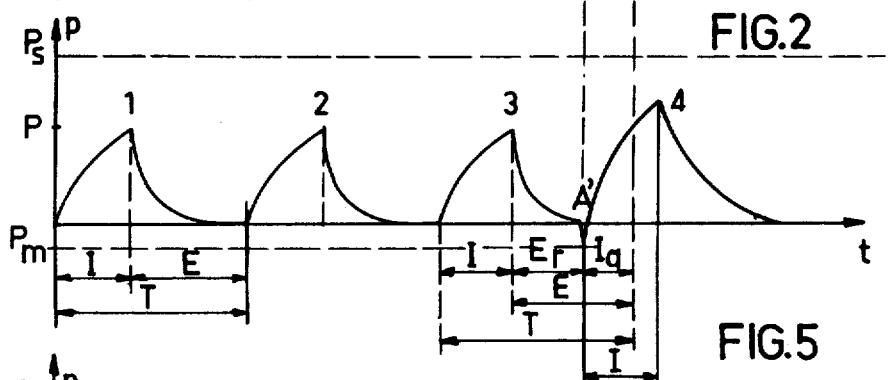

If the patient makes an effort to inhale, when the ventilation becomes inadequate, a negative pressure occurs in the branch 31 of the utilisation circuit, which appears at A' in FIG. 5 (corresponding to point A of FIG. 1). This negative pressure detected by the pickup 81 is converted proportionately into an electrical voltage which is received by the comparators 820a and 820b. This voltage is compared to the references voltages preset by the control elements 821a and 821b, and as soon as it reaches the value of the reference voltage set by 821a and corresponding to Pm, the comparator 820a transmits an electrical signal to the clock 51 via the conductor 823a and to the subtractor 826a via the conductor 827a. The clock 51 drives the control element 52 so that it triggers a premature inhalation stage. The exhalation period is consequently shortened to a true value Er which is shorter than the exhalation period E preset by the device 50. The subtractor 826a determines the difference between the stored exhalation period E which should have occurred, and the exhalation period Er actually produced. The difference between these two periods enables the subtractor 826a to operate the opening of the electromagnetic valve 62 via the amplifier 830a, for a period E−Er=Ia and to supply the bladder 41 with make-up breathable gas. The level of energy in the bladder 41 rises, which implies an increase of the inhalation flow. The ventilation is then performed according to cycles 3 and 4 of FIG. 5. The cycle 4 overlaps cycle 3 and its peak pressure exceeds the value P of the preceding cycles.

If, on the contrary, the ventilation becomes excessive due to an obstruction of the patient's respirator tracts, this leads to a pressure rise in the utilising circuit. This pressure, detected by the pickup 81, is converted into a proportional electrical voltage which is received by the comparators 820a, 820b. As soon as this voltage reaches the reference value preset by 821b and corresponding to PM, the comparator 820b transmits an electrical signal to the clock 51 via the conductor 823b and to the subtractor 826b via the conductor 827b. The clock 51 drives the control element 52 so that it triggers a premature exhalation stage. The inhalation stage is consequently decreased to a true value Ir shorter than the inhalation period I present by the device 50. The subtractor 826b also determines the difference between the inhalation period I stored and which should have occurred, and the inhalation period Ir actually produced. The difference between the two periods enables the subtractor 826b, acting via the amplifier 830b, to operate the opening of the electromagnetic valve 72 for a period I−Ir=V, in such manner that a part of the breathable gas stored in the bladder 41 is dumped to the outside, causing its partial decompression. The level of energy in the bladder 41 decreases and the inhalation flow rate consequently equally decreases.

Figure 6:
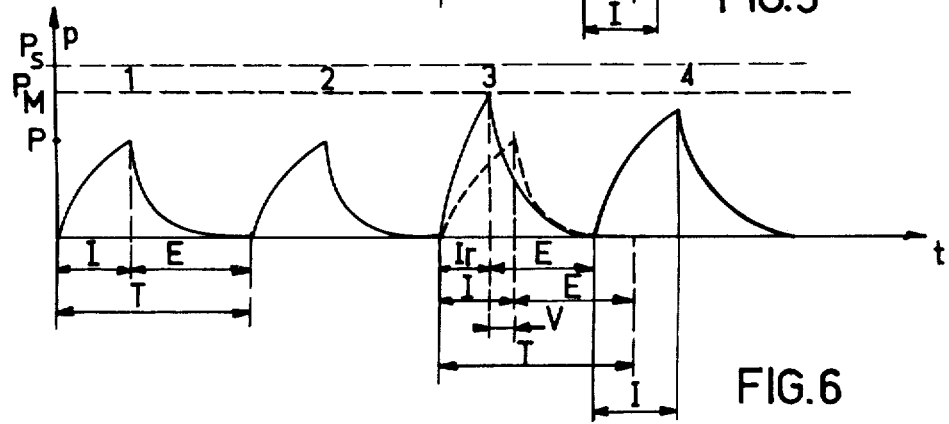

The inhalation and exhalation cycles then display the form depicted by cycles 3 and 4 of FIG. 6. The peak pressure of the cycle 3 reaches the value PM, whereas the peak pressure of the cycle 4 reverts to a value lower than PM due to the decompression of the bladder 41.

Numerous modifications may be made in the arrangement of the embodiment described and illustrated without in any way departing from the scope of the invention as defined by the appended claims.

What I claim is:

1. In a respirator for the artificial ventilation of the pulmonary tracts of a user in accordance with a cycle of inhalation and exhalation stages of the kind comprising supply circuit means delivering a breathable gas, utilisation circuit means including an inhalation branch and an exhalation branch provided with an exhalation valve, breathable gas accumulator means communicating with said supply and utilisation circuit means and forming a reserve buffer of said breathable gas, distributor means connected to said supply circuit means and comprising an inhalation valve in communication with said inhalation branch for selectively admitting said breathable gas thereto, an accumulator valve and a non-return valve both of which are disposed between the inhalation valve and said accumulator, a cyclic action control device which controls said inhalation valve, said exhalation valve, and said accumulator valve according to a predetermined programme and which is arranged to direct the breathable gas coming from the supply circuit means and from the accumulator means towards said inhalation branch during the inhalation stages, and to direct the breathable gas coming from said supply circuit means towards said accumulator during the exhalation stages; the improvement comprising, in combination with the foregoing, auxiliary makeup circuit means for supplying a complement of breathable gas to the utilisation circuit means, discharge circuit means for selectively withdrawing a part of the breathable gas in advance of said utilisation circuit, and ventilation corrector circuit means sensing changes in pressure in said inhalation branch and responsive to the durations of the inhalation and exhalation stages to alter such durations accordingly, with said ventilation corrector circuit means acting on said auxiliary makeup circuit means and said discharge circuit means to cause such means to make up or to withdraw said breathable air in dependence upon said changes in pressure and changes in said durations.

2. A respirator according to claim 1, wherein said auxiliary make-up circuit means comprises a pipe connecting the supply circuit to said accumulator and provided with an electromagnetic valve and with a calibrated orifice.

3. A respirator according to claim 2, wherein said discharge circuit means comprises a venting pipe in communication with said accumulator means and provided with an electromagnetic valve.

4. A respirator according to claim 3, wherein said connecting and venting pipes are in communication with said accumulator means to cooperate with upflow and downflow, respectively, of said non-return valve for the direction of flow of the breathable gas from said accumulator means towards said inhalation branch.

5. A respirator according to claim 4, wherein said ventilation corrector circuit means comprises a pressure pickup arranged to supply electrical signals in dependance upon the pressure in said inhalation branch, an electronic calculator connected to said pickup as well as to said cyclic action control device and a controller driven by said calculator and arranged to operate the opening and closing of said electromagnetic valves.

6. A respirator according to claim 5, wherein said pressure pickup is of the piezo-resistive type and is arranged to deliver a voltage proportional to the pressure it receives from said inhalation branch.

7. A respirator according to claim 6, wherein said electronic calculator comprises comparator circuits, each having a plurality of input terminals one of which is connected to said pickup and another of which is connected to a respective control element arranged to supply a respective one of two reference valves, the one being a minimum, the other a maximum, said comparators driving said cyclic action control device so that it triggers an inhalation stage or an exhalation stage when the electrical voltage supplied by said pickup reaches the aforesaid minimum value or maximum value.

8. A respirator according to claim 7, wherein said calculator comprises memory circuits for storing inhalation and exhalation periods (I and E) each associated with the inhalation and exhalation stages and preset by its respective control element, and subtractor circuits each having a plurality of input terminals one of which is connected to an associated one of said memory circuits and another of which is connected to an associated one of said comparator circuits, which comparator circuits produce modified inhalation and exhalation periods ($I_r$ and $E_r$) which are shorter than said inhalation and exhalation periods (I and E), respectively, determined in dependence upon said minimum and maximum reference values, said subtractor circuits providing difference values ($I-I_r$ and $E-E_r$) driving said cyclic action control device so that it controls of opening of the respective electromagnetic valves in dependence upon the difference values ($I-I_r$ and $E-E_r$).

9. A respirator according to claim 8, wherein said controller comprises amplifier means having a plurality of input terminals which are connected to said subtractor circuits and a plurality of output terminals which are connected to said electromagnetic valves.

* * * * *